United States Patent [19]

Lee

[11] Patent Number: 5,190,540

[45] Date of Patent: Mar. 2, 1993

[54] THERMAL BALLOON ANGIOPLASTY

[75] Inventor: Benjamin I. Lee, Washington, D.C.

[73] Assignee: Cardiovascular & Interventional Research Consultants, Inc., Indianapolis, Ind.

[21] Appl. No.: 765,326

[22] Filed: Sep. 25, 1991

Related U.S. Application Data

[63] Continuation-in-part of Ser. No. 535,022, Jun. 8, 1990, abandoned.

[51] Int. Cl.$^5$ .............................................. A61B 17/36
[52] U.S. Cl. ........................................ 606/28; 606/27; 606/192; 606/194
[58] Field of Search ........................... 606/7, 27-31, 606/41, 42, 192, 194; 604/96

[56] References Cited

U.S. PATENT DOCUMENTS

| 4,955,377 | 9/1990 | Lennox et al. | 606/27 |
| 5,009,662 | 4/1991 | Wallace et al. | 606/192 |
| 5,032,113 | 7/1991 | Burns | 606/194 X |
| 5,035,694 | 7/1991 | Kasprzyk et al. | 606/28 X |
| 5,041,089 | 8/1991 | Mueller et al. | 606/28 X |
| 5,057,106 | 10/1991 | Kasevich et al. | 606/33 |
| 5,092,841 | 3/1992 | Spears | 606/194 X |

FOREIGN PATENT DOCUMENTS

9103207  3/1991  World Int. Prop. O. ............ 606/28

OTHER PUBLICATIONS

Lee et al., "Thermal Compression and Molding of Atherosclerotic Vascular Tissue with Use of Radiofrequency Energy: Implications for Radiofrequency Balloon Angioplasty", *Journal of the American College of Cardiology*, vol. 13, No. 5, Apr. 1989, pp. 1167-1175.

*Primary Examiner*—Peter A. Aschenbrenner
*Attorney, Agent, or Firm*—Cushman, Darby & Cushman

[57] ABSTRACT

A method for remodeling a body lumen, such as a coronary artery, having a stenosis to expand the stenosis comprising the steps of increasing the temperature of the body lumen and stenosis at the region of the stenosis for a time period and to a temperature level sufficient to cause a change in the stenosis and body lumen region from a relatively solid state into a softer and more moldable state and thereafter expanding the stenosis and the body lumen region while in the softer and more moldable state to thus reduce the tendency to fracture during expansion, and reducing the temperature of the stenosis and body lumen region while maintaining the expansion for a time period and to a temperature level sufficient to re-establish the relatively solid state thereof so as to increase the tendency to maintain the stenosis and body lumen region in the expanded condition. An improved heat applying balloon catheter is provided including passages for displacing the heated balloon inflating liquid with a cooling liquid to carry out the method.

20 Claims, 2 Drawing Sheets

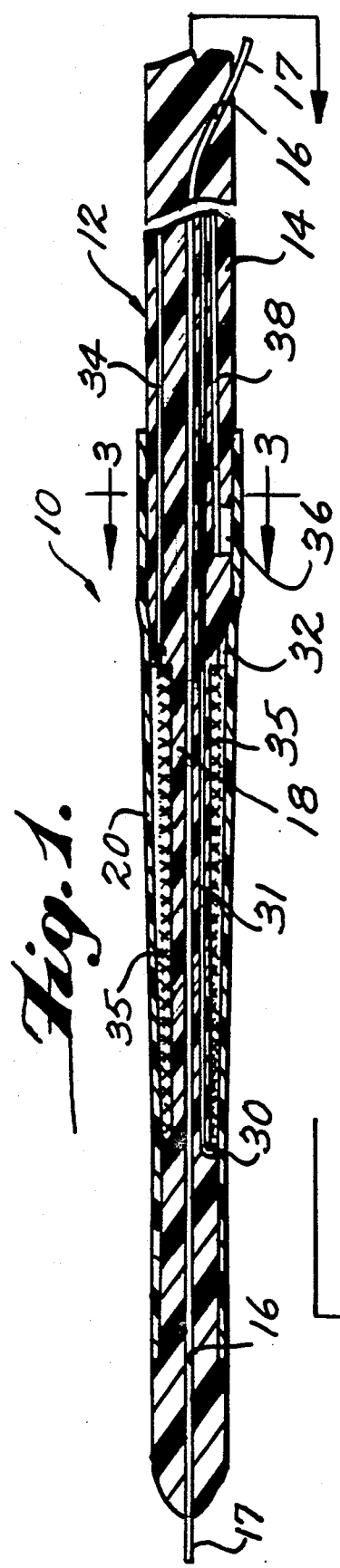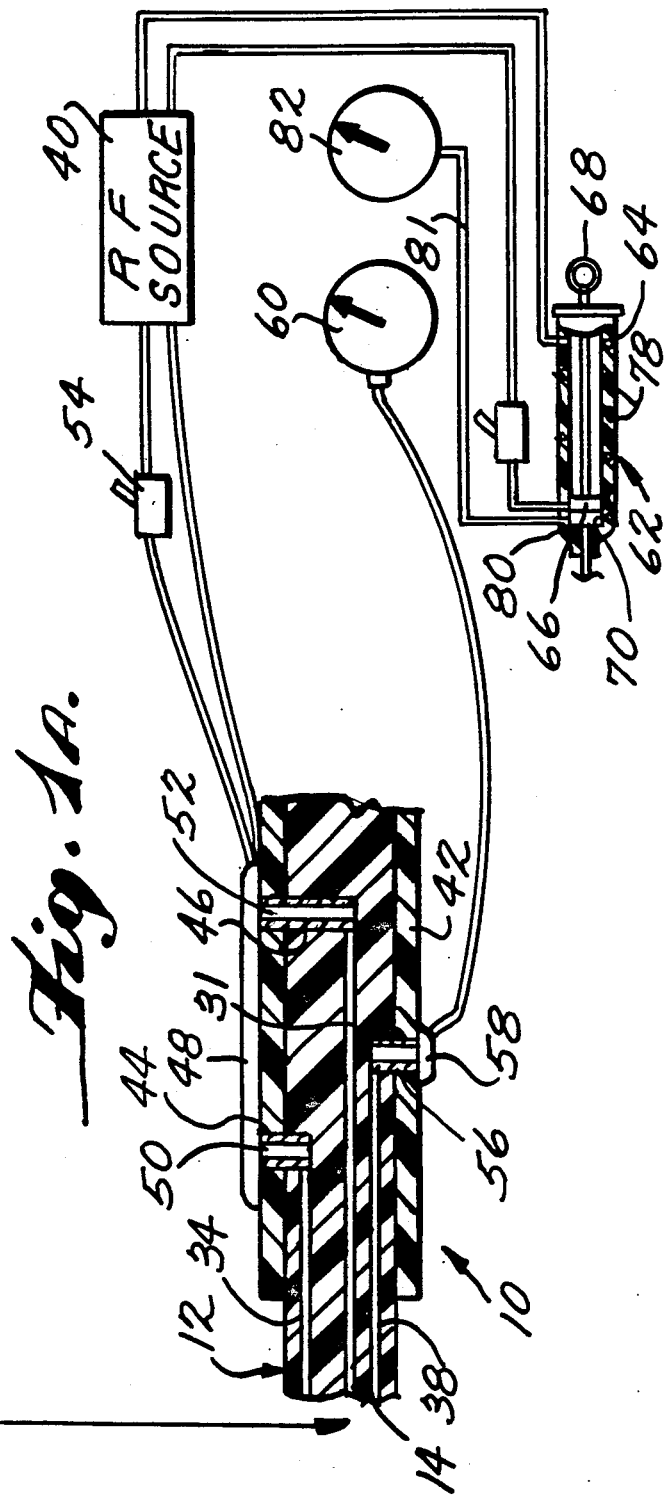

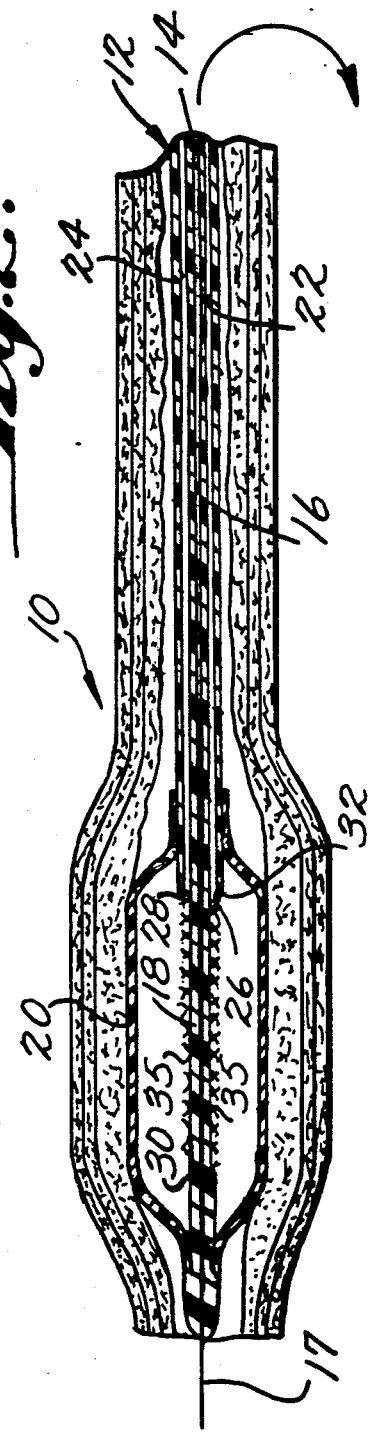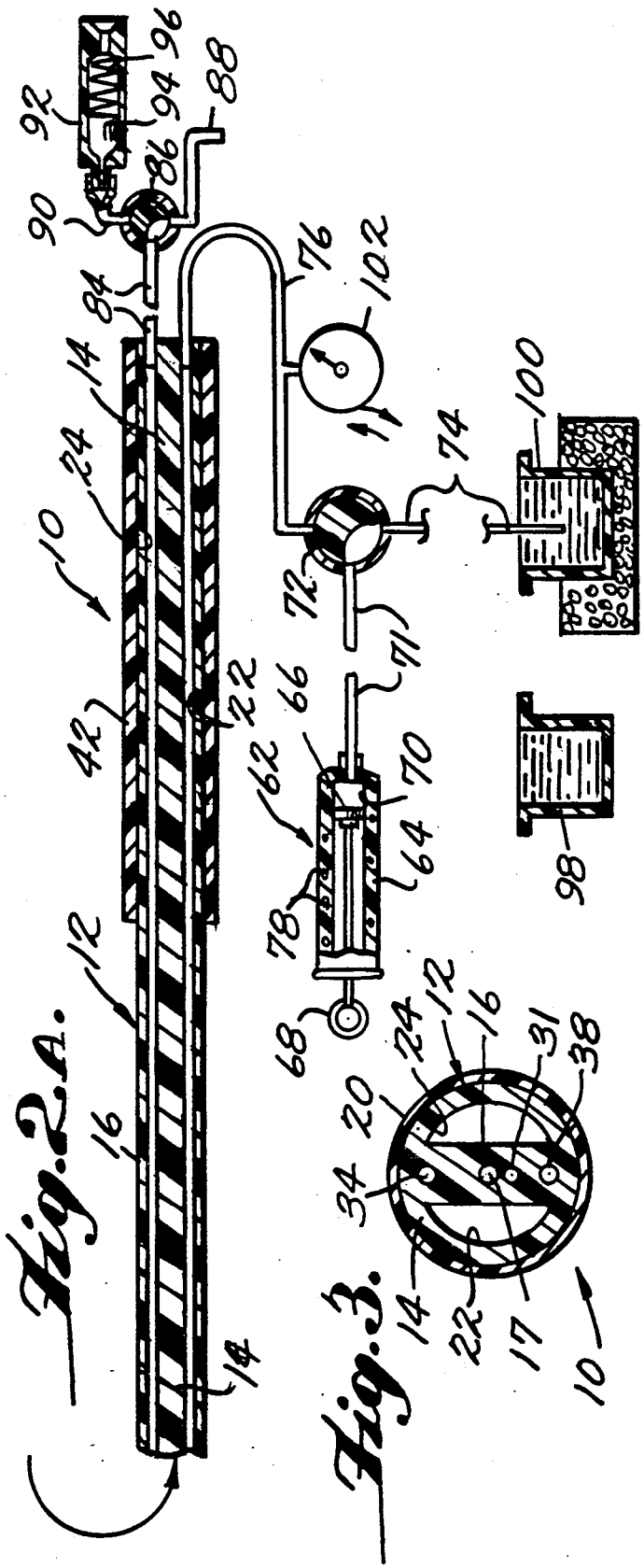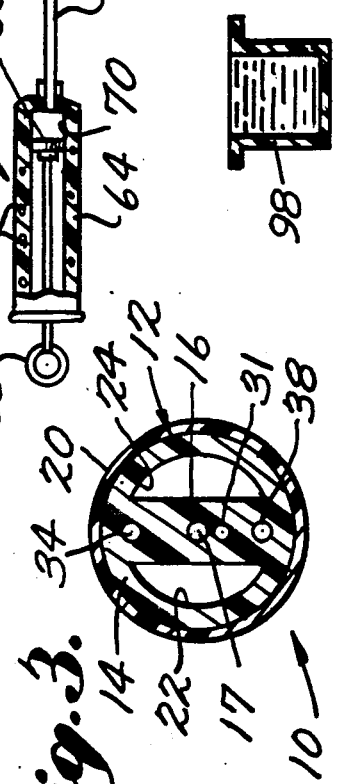

THERMAL BALLOON ANGIOPLASTY

This application constitutes a continuation-in-part of my earlier U.S. patent application No. 07/535,022, filed Jun. 8. 1990, for Thermal Balloon Angioplasty, which application is now abandoned.

This invention relates to angioplasty and, more particularly, to improvements in a method and apparatus for preventing abrupt reclosure and restenosis after treatment.

Ischemic heart disease is a consequence of atherosclerotic coronary artery narrowing and is responsible for significant debility and mortality due to angina, myocardial infarction, congestive heart failure and sudden death. Percutaneous transluminal coronary angioplasty (PTCA) has been shown to be an effective treatment modality for patients with symptomatic coronary artery disease, although its effect on overall mortality remains unestablished. During cardiac catheterization, an inflatable balloon is threaded into the affected coronary artery and positioned at the site of coronary artery narrowing. Inflation of the balloon results in expansion of the narrowed lumen by a combination of stretching, cracking, breaking and tearing of the vessel wall and atherosclerotic plaque. Despite an initially successful dilation, vessel elastic recoil, intimal flaps, thrombus formation and smooth muscle fibroproliferation, are thought to contribute to the significant acute and chronic reclosure rate following standard balloon angioplasty.

Although there are several new devices capable of recanalizing stenotic arteries, none have yet been proven effective in preventing restenosis. It has been hypothesized that the incidence of acute closure and chronic restenosis is reduced by thermal sealing of the intimal flaps created during standard balloon angioplasty. U.S. Pat. No. 4,799,479 discloses a heating technique, in which the disrupted tissues of the plaque and arterial wall produced by balloon inflation are heated in order to fuse together fragmented segments of tissue, to coagulate blood trapped within dissected tissue planes and within fissures created by wall fracture. Upon subsequent balloon deflation, a smooth, cylindrically-shaped channel is indicated to result. The thermal energy is applied after the initial balloon inflation or after subsequent balloon inflations so that the vessel is disrupted by balloon inflation and subsequently thermally fused.

The '479 patent further indicates that thermal fusion reduces elastic recoil of the arterial wall, which often occurs following conventional PTCA. Moreover, the '479 patent indicates that abrupt closure following the thermal treatment during PTCA is prevented since upon balloon deflation blood is unable to enter dissected tissue planes within the arterial wall and the incidence of restenosis is reduced because of more favorable flow patterns produced by the smooth lumen and because the fused necrotic elements of the arterial wall are incapable of proliferation in response to the initial injury sustained during balloon inflation. Finally, the '479 patent notes that, while it has been suggested that the patent smooth muscle cell, the principal cell type within the plaque and normal arterial wall, proliferates in response to any form of injury and contributes to the restenosis lesion, thermal destruction of the smooth muscle cell provided by the heating technique tends to prevent this response. However, clinical trials have subsequently shown an increased incidence of restenosis following laser thermal balloon angioplasty compared to standard balloon angioplasty, likely due to extensive laser-induced thermal injury resulting in a heightened fibroproliferative response. Since the magnitude and duration of tissue heating determines the extent of tissue thermal injury, extensive thermal injury occurs due to excessive tissue temperatures (greater than 90° C.), prolonged tissue exposure, or both.

U.S. Pat. No. 4,998,933 describes the selective heating of an atherosclerotic mass in order to soften the occlusive mass allowing it to be more readily crossed by the balloon catheter and subsequently dilated. The atherosclerotic mass is heated by passing high frequency voltage between an array of electrodes located on the guiding wire and catheter shaft. The heating mechanism is not well described and other than softening the plaque, no other additional information is disclosed regarding the extent or consequences of heating the atherosclerotic mass prior to passage of the balloon catheter.

Lastly, clinical trials to date have shown that intraluminal stents, atherectomy devices and lasers do not prevent restenosis; and furthermore, have demonstrated that any injury to vessel wall be it mechanical or thermal may incite the process of restenosis. Thus, a means of achieving an adequate vessel lumen with minimal vessel wall trauma will likely yield the best short and long-term clinical results.

The present invention is based upon the observation that vascular tissues, comprised of collagen and atherosclerotic plaque, reversibly change in consistency and pliability relative to changes in tissue temperature. We have observed that when an atherosclerotic vessel segment is heated, the fatty or lipid components liquify and the collagenous components become more pliable. This process is rapidly reversed when the vessel is quickly cooled. Thus, an atherosclerotic stenosis and the surrounding arterial tissue can be mechanically dilated with much less fracturing and tissue trauma when expansion occurs while the stenosis and arterial tissue are at an elevated temperature condition. The observed phenomena is believed to exist because the high fat content present changes from a substantially solid state to a semi-solid or substantially softer more moldable state. Conventional balloon angioplasty accomplishes mechanical expansion of the stenosis and surrounding arterial tissue without temperature change. U.S. Pat. No. 4,799,479 teaches that the fracturing which occurs by mechanical expansion without temperature change can be repaired by fusing the fractures together with heat. The present invention deals with the fracturing problem in an entirely different manner. Rather than to fuse the fractures which occur by mechanical expansion at ambient temperature, the present invention attempts to minimize the creation of fractures and limit mechanical trauma to the vessel wall by effecting mechanical expansion only after the stenosis and surrounding arterial tissue have been elevated in temperature to a level and for a time sufficient to cause the aforesaid change to a softer and more moldable state.

The apparatus and method of the present invention enables angioplasty to be practiced in a manner which causes less barotrauma or mechanical injury and, more importantly, less thermal injury to the vessel. This is because the stenosis and tissue is rapidly heated prior to and rapidly cooled during full balloon expansion. Moreover, by having both rapid heating and rapid cooling immediately available, thermal damage can be effectively controlled by minimizing the magnitude and duration of heat exposure to tissue. All of these advantages help prevent acute occlusion while minimizing the stimulus for chronic restenosis.

It is a further important feature of the present invention to re-establish by rapid temperature reversal the original more solid state of the stenosis and surrounding material as one achieves maximal mechanical dilation and prior to reducing the mechanical dilation so as to minimize heat exposure and increase the tendency of the stenosis and surrounding tissue to remain in its expanded condition. In view of the desirability to minimize the time period of total occlusion by the inflated balloon, it is greatly preferred to positively cool the stenosis and arterial tissue at a rate greater than that would occur by passive cooling and faster than the tissue temperature half-life. Preferably, positive cooling is accomplished by displacing the heated balloon inflation liquid with a cooling liquid. We have observed that atherosclerotic vessels more optimally retain their dilated shape when rapidly heated and rapidly cooled while stretched in the shape of an angioplasty balloon, as compared to vessels allowed to cool by heat removal resulting from balloon deflation and withdrawal. The cooling feature of the present invention improves the chances of successfully achieving satisfactory vessel expansion with only one balloon inflation/deflation cycle in comparison to conventional PTCA which often requires several balloon inflations to achieve the desired degree of vessel dilation. Stated differently, by applying heat to an atherosclerotic narrowing prior to significant balloon dilatation an rapid cooling during maximal balloon expansion, vessel dilatation occurs while atherosclerotic tissues are softened and less prone to tearing. Rapid cooling while the balloon is maximally inflated allows the heat softened atherosclerotic tissue and collagen to congeal in the shape of the inflated balloon minimizing tissue elastic recoil and tissue thermal injury, factors which contribute to abrupt vessel closure and late restenosis.

Rapid heating and cooling capacity may also be used to deliver thermoplastic materials within the coronary artery. Thermoplastic materials which are liquid or viscous when heated and which harden when rapidly cooled and perhaps containing antiproliferative agents can be delivered in a heated viscous or gel-like form via a porous balloon to the inner surface of the arterial wall. With the balloon fully expanded and cooled, the thermoplastic material is hardened and molded against the vessel wall creating a protective layer against circulating blood elements as well as a functional and antiproliferative endoluminal stent.

The method and apparatus of the present invention is most importantly applicable to improve PTCA of coronary arteries, however, the improved method can also be applied to atherosclerotic arteries located elsewhere, such as the renal, femoral and popliteal arteries as well as carotid arteries and to any body lumen or elongated cavity where a restriction or stenosis may present a problem and remolding in accordance with the principles of the present invention would alleviate the problem, as, for example, the urinary tract, the biliary tract, Fallopian tubes, etc.

Accordingly, in its broadest aspects, it is an object of the present invention to provide a method for carrying out balloon catheter angioplasty within an artery having a stenosis comprising the steps of positioning the balloon of the catheter within the stenosis of the artery, increasing the temperature of the stenosis and artery surrounding the balloon prior to the inflation of the balloon to an inflation extent sufficient to cause outward expansion of the stenosis, for a time period and to a temperature level sufficient to cause a change in the stenosis and surrounding artery from a relatively solid state into a softer and more moldable state and, thereafter, increasing the inflation of the balloon so that outward expansion occurs with the stenosis and artery in said softer and more moldable state to thus reduce the tendency to fracture during expansion while rapidly reducing the temperature of the stenosis and surrounding artery and maintaining the expansion by balloon inflation for a time period and to a temperature level sufficient to re-establish the relatively solid state thereof so as to increase the tendency to maintain the stenosis and artery in the expanded condition, and then deflating the balloon and withdrawing the catheter.

U.S. Pat. No. 4,799,479 discloses several different arrangements for providing heat in conjunction with pressurization. The preferred heating arrangement is to heat the tissue directly by laser light which passes through the liquid used to inflate the balloon without directly heating the liquid, so that heat is added to the liquid only by conduction via the heated vessel wall. Another arrangement is the reverse of the preferred arrangement wherein the heat is applied only to the liquid used to inflate the balloon without directly heating the tissue which is heated only by conduction. Another arrangement results in directly heating both the tissue and liquid.

The principles of the present invention can be carried out utilizing any of the various heating arrangements disclosed in U.S. Pat. Nos. 4,799,479, 4,955,377, 4,754,752. A preferred heating arrangement of the present invention is the arrangement in which the heat is applied directly to the liquid and not to the tissue so that the tissue is heated by conduction. This heating arrangement is preferred because tissue temperature can be more accurately measured and controlled and the chances of tissue damage, as compared with, for example, laser heating which can produce tissue temperatures in excess of several hundred degrees Centigrade, is less. An arrangement of this type is illustrated in the FIG. 4 embodiment of U.S. Pat. No. 4,799,479 which indicates that electrical resistance heating is used without illustrating a complete circuit and electrical source. An alternative disclosure of conductive electrical resistance heating arrangement utilizing a radio-frequency electrical source and its advantages is disclosed in an article entitled "Thermal Compression and Molding of Atherosclerotic Vascular Tissue with Use of Radio-Frequency Energy: Implications for Radio-Frequency Balloon Angioplasty" by Lee et al., printed in the April 1989 issue of the Journal of the American College of Cardiology, Vol. 13, No. 5 and U.S. Pat. No. 4,955,377 by Lennox et al. The '377 patent disclosure indicates that pressurization can be maintained for a period after the heat is no longer applied, during which period, the heat will dissipate somewhat and the temperature of the tissue is allowed to cool down. This procedure is in contrast with the disclosure of the '479 patent which seems to equate deflation with heat application removal.

U.S. Pat. No. 4,754,752 discloses a method of convective heating of inflation medium within the balloon utilizing laser energy to heat a radiant heating block within the balloon. However, this arrangement could allow thermal damage to the balloon skin during heating and the heating element would make the balloon tip bulky and inflexible.

The cooling feature of the present invention is based upon the positive application of rapid cooling during maximum balloon inflation immediately after heat application removal and preferably during an increase in balloon expansion. Preferably, the cooling is positively provided by replacing the heated liquid with a cooled liquid having a temperature below room temperature, within a range of 0° to 38° preferably 15° to 35° and preferably approximately 25°, with the preferred temperature of the cooling liquid, the tissue temperature can be rapidly cooled to room temperature in less than approximately 5 seconds allowing the heat softened tissues to stretch than congeal in the shape of the expanded balloon. It is an object of this invention that the inflated balloon is filled with cold fluid under constant positive and maximal pressurization.

Another object of the present invention is the provision of an angioplasty apparatus of the type which includes a catheter comprising an elongated body of flexible material having a distal end portion and a balloon on the distal end portion of the catheter body. The catheter body has an inlet passage extending longitudinally therethrough from an inlet position therein to an outlet position at the distal end portion and an outlet passage extending longitudinally therethrough from an inlet position at the distal end portion to an outlet position. The inlet passage has an outlet opening at the outlet position communicating with the interior of the balloon through which pre-heated liquid under pressure in the inlet passage can enter the interior of the balloon. The outlet opening of the 'inlet passage consists of a heated braided wire tube through which incoming liquid is further heated as it enters the interior of the balloon. The braided wire tube is insulated to prevent thermal damage to the catheter body. The braided wire tube is heated by electrical or RF energy supplied through thin wires which extend within the flexible material of the catheter from the distal end portion for selectively connecting a remote source of electrical energy with the heated braided wire tube. An identical energy source heats both the incoming fluid within a device connected to the catheter and the braided wire tube. The outlet passage has an inlet opening at the inlet position communicating with the interior of the balloon through which liquid under pressure within the balloon can pass from the balloon into the outlet passage. A liquid pumping system device is operatively connected with the catheter at the inlet and outlet positions of the inlet and outlet passages for (1) pre-heating and introducing a balloon inflating and heating liquid within the inlet passage with an initial pressure sufficient to establish a liquid pressure within the balloon sufficient to inflate the same into contact with an area of stenosis within an arterial region within which the distal end portion of the catheter is engaged while the heating wires connect the electrical energy source to the heating braid wire tube to operate the same to further heat the liquid under pressure within the balloon to a predetermined temperature sufficient to conduct sufficient heat to the arterial region to change the tissue in the arterial region and stenosis from a relatively solid state into a softer and more moldable state so that while therein an increase in the liquid pressure within the balloon increases the inflation of the balloon and expands the area of stenosis within the arterial region within a first predetermined time, (2) following the expiration of the first predetermined time displacing the balloon inflation and heating liquid within the inlet passage and the interior of the balloon outward through the outlet passage with a cooling liquid while maintaining an inflating pressure within the interior of the balloon for a second predetermined time sufficient to change the tissue in the arterial region and stenosis into a relatively solid state to thereby enhance the formation of a smooth inner wall in the arterial region, and (3) following the expiration of the second predetermined time relieving the pressure of the liquid within the interior of the balloon sufficient to deflate the same for removal from the arterial region.

While the principles of the present invention are applicable to movable or fixed wire catheter arrangements, it is also preferable to utilize a monorail guide wire design so as to allow ease of exchange with catheters of different sizes.

Another object of the present invention is the provision of angioplasty apparatus which is simple in construction, effective in operation, economical to manufacture.

These and other objects of the present invention will become more apparent during the course of the following detailed descriptions and appended claims.

The invention may best by understood with reference to the accompanying drawings wherein an illustrative embodiment is shown.

DETAILED DESCRIPTION OF THE DRAWINGS

FIG. 1 is a vertical sectional view of the distal end of a angioplasty catheter embodying the principles of the present invention, showing the balloon in a deflated condition;

FIG. 1A is a view similar to FIG. 1 showing the angioplasty apparatus of the present invention connected with the opposite end of the catheter apparatus of FIG. 1;

FIG. 2 is a view similar to FIG. 1 showing the balloon inflated, the section being taken along a plane displaced 90° with respect to the sectional plane of FIG. 1;

FIG. 2A is a view similar to FIG. 1A associated with FIG. 2; and

FIG. 3 is a sectional view taken along the line 3—3 of FIG. 1.

Referring now more particularly to the drawings, there is shown therein an angioplasty apparatus, generally indicated at 10, which embodies the principles of the present invention. As shown, the apparatus 10 includes an elongated catheter, generally indicated at 12, in the form of an elongated body 14 of flexible material (e.g. polyethylene or polyester) molded so that the distal end has a central opening 16 therein which exits laterally, as shown in FIG. 1, at a position approximately one third of the longitudinal extent of the body 14. Opening 16 establishes the catheter 10 as a monorail catheter. The guide wire 17 extends longitudinally outwardly from a distal end portion 18 of the catheter body 14 and forms a guide wire for the catheter. A balloon 20 structure in the form of an annular wall is mounted over the distal end portion 18 of the catheter body 14 of flexible material and the adjacent portion of the guide wire 17.

The catheter body 14 is formed with an inlet passage 22 extending therethrough and a generally parallel outlet passage 24 extending therethrough. As best shown in FIG. 1, the inlet passage 22 extends to an outlet position at the distal end portion 18 of the catheter body 14 and has an outlet opening 26 which communicates with the interior of the balloon 20. The outlet passage 24 extends through the catheter body from an inlet position at the distal end of the catheter body where there is provided an inlet opening 28 which communicates with the interior of the balloon 20.

A distal electrical connector band 30 is formed on the distal end of the catheter body 14 at a position within the distal portion of the balloon 20. Electrical connector 30 is connected with one end of an electrical wire 31 which extends within the flexible material of the catheter body 14 from the distal end to the opposite end thereof. A spaced proximal electrical connector 32 is formed on the exterior of the catheter body 14 at a position within the proximal end of the interior of the balloon 20. The proximal electrical connector 32 is electrically connected with one end of an electrical wire 34 which extends within the flexible material of the catheter body 14 from the distal end to the opposite end thereof. Electrically connected between the connectors 32 and 34 is a heating element preferably in the form of a braided stainless steel wire sleeve 35. Sleeve 35 is disposed in surrounding relation to the central portion of the distal end 18 of the catheter body 14 with the proximal end held by the proximal band 32 to receive fluid therein from the outlet opening 26.

A temperature sensing element in the form of a thermistor 36 is provided on the exterior of the catheter body 14 in a position within the proximal interior of the balloon 20. The thermistor 36 is directly connected to a lead wire 38 which, like the wires 31 and 34 extends through the flexible material of the catheter body 14 from the distal end portion 18 to the opposite end thereof.

FIG. 1A illustrates the connection of the proximal end of the wire 31, which is connected at its distal end with the distal connector 30 and the proximal end of the wire 34, which is connected at its distal end to the proximal connector 32, to a suitable source of electrical energy 40. As shown, the source 40 is schematically illustrated as a source of alternating current electricity having a cycle at radio frequency within a range of 100 khz to mhz, for example, preferably 650 khz. As best shown in FIG. 1A, at the opposite end of the catheter body 14 there is provided a surrounding handle 42 within which electrical sockets 44 and 46 are mounted in connection with the adjacent ends of the wires 31 and 34 respectively. An electric plug 48 having two prongs 50 and 52 is adapted to engage within the sockets 44 and 46 to selectively connect the source 40, through a manual switch, schematically illustrated at 54, with the heating sleeve 35 through wires 31 and 34. In addition, it will be noted that a third socket 56 is connected to the end of the wire 38 which is connected with the thermistor 36. A plug 58 is adapted to engage within the socket 56 to connect the thermistor 36 with a temperature gauge 60.

Referring now more particularly to FIG. 2A, there is shown therein a pump mechanism in the form of a manually actuated syringe, generally indicated at 62. In the example illustrated in the drawings, the syringe 62 includes a cylindrical syringe chamber wall 64 within which is mounted a syringe piston 66 movable within the chamber 64 by piston rod 68. The variable space 70 within the cylindrical chamber wall 64 which is defined by the position of the piston 66 therein is connected via a tube or line 71 to a manually actuated valve 72 which serves to connect the chamber space 70 when in one position with a suction tube or line 74, and when in a second position with a tube or line 76 which communicates with the inlet of the inlet passage 22.

As shown, the cylindrical chamber wall 64 is formed with a resistance heating coil 78 which can be energized by electrical source 40 selectively by actuating manual switch 79 when switch 79 is on by which liquid within the space 70 can be heated. A thermistor 80 is also provided in the cylindrical chamber wall operable through electrical lead 81 to register the water temperature within space 70 on a temperature gauge 82.

The outlet of the outlet passage 24 is connected with a tube or line 84 which leads, in turn, to a manual valve 86. In one position of valve 86, liquid within the line 84 is discharged through a line 88. In a second position of valve 86, liquid within the line 84 is directed into line 90 which, in turn, leads into a chamber 92 which is controlled by a valve member 94 normally closed by a spring 96. The valve member 94 and spring 96 within chamber 92 thus constitute a check valve which permits passage of liquid into the chamber 92 from the outlet passage 24 so long as the pressure of the liquid is at a predetermined level. An exemplary pressure is 16 psi which is the maximum pressure of the balloon when in its maximum expansion which is limited by the structure of the balloon wall in accordance with conventional practice.

While the drawings illustrate a preferred manual switch 54 and visual gauges 60 and 82, it will be understood that a more automatically controlled circuit may be provided of the type utilized in the aforesaid U.S. Pat. No. 4,955,377. It will also be understood that the syringe 62 may be motor actuated in accordance with the disclosure contained in the '377 patent. For background purposes, the disclosure of the '377 patent is hereby incorporated by reference into the present specification.

The catheter 10 is a monorail catheter and is prepared for insertion with a negative pressure prep syringe (not shown) in accordance with conventional procedures and inserted within the patient in accordance with conventional procedures. At the end of the insertion procedure, the distal end portion 18 of the catheter 10 including balloon 16 is within the stenosis.

Prior to insertion, the syringe 62 is also prepared by turning valve 72 into the position shown in FIG. 2A and communicating line 74 with a source of liquid 98 as, for example, a water solution having a contrast dye therein (e.g., Hexabrix ®). The piston 66 of the syringe 62 is withdrawn by the piston rod 68 to fill space 70 with liquid. Switch 79 is moved into its on position to electrically energize the heating coil 78 of the syringe 62. The liquid in space 70 is preheated to a preheated temperature within the range of 40° to 100° C., a preferred preheated temperature being 70° C. as determined by gauge 82.

As soon as the balloon has been positioned within the stenosis, the prep syringe is disengaged and the proximal ends of passages 22 and 24 are connected with lines 76 and 84 respectively. With valve 86 disposed in the position shown in FIG. 2A, the piston rod 68 of the syringe 62 is actuated inwardly. Actuation of the piston rod 68 in a direction to move the piston 66 inwardly causes preheated inflating and heating liquid to move through the inlet passage 22 and into the balloon 20 through outlet opening 26. The preheated liquid within the balloon 20 is allowed to pass through the inlet opening 28 into the outlet passage 24 where it finally reaches discharge tube 88. The resistance to flow through the outlet passage 24 and discharge tube 88 is such that sufficient liquid is retained in the balloon 20 to insure that it is spaced from the sleeve 35. As soon as a discharge of liquid is noted from tube 88, valve 86 is moved into a position communicating lines 84 and 90 and switch 54 is turned on to energize the braided sleeve 35.

In accordance with usual practice, the dye within the liquid enables the doctor to follow the movement of the balloon 20 on a suitable scope. Consequently, a continued actuation of the piston rod 68 in a direction to move the piston 66 inwardly causes preheated inflating and heating liquid to move through the outlet opening 26 into the balloon 20 within the energized sleeve 35 to pass therethrough and inflate the balloon 20 into contact with the stenosis which relationship can be readily observed on the scope. The initial inflation pressure (which does not expand the stenosis) corresponds with a reading of approximately 4 psi or less on a pressure gauge 102 in line 76. As soon as contact is made, the valve 72 is turned to a third position wherein the liquid is trapped within the line 76 and the inlet passage 22. In this way, the energized sleeve heating element 35 serves to rapidly raise the temperature of the preheated liquid which has reduced in temperature somewhat.

As previously indicated, the source of electrical energy utilized is an alternating current having a cycle of radio frequency within the range 100 khz to 1 mhz with an exemplary preferred frequency being approximately 650 khz. As soon as a temperature within the range of 40° C. to 100° C. with an exemplary preferred temperature of approximately 70° C. is noted on the temperature gauge 60 as determined by the thermistor 36, the switch 54 is thrown to terminate the flow of electrical current. A reading of 70° C. on the thermistor temperature gauge 60 has been previously calibrated to correspond with a tissue temperature surrounding the balloon of approximately 70° C. Normally, this temperature is achieved in approximately 10 to 20 seconds, preferably 15 seconds. This elevated temperature level changes the stenosis and arterial region surrounding the balloon 20 from a generally solid state into a softer more moldable state.

During the heating procedure, valve 72 is moved into its first position and the piston 66 is actuated a few times to mix the residual liquid within the space 70 and the suction line 74 with a cooling liquid, which is the same as the inflating and heating liquid held within a supply container or source 100. When the cooling liquid is at a temperature within the range of 0° to 38° C., or an exemplary preferred temperature of approximately 25° C., a charge of cooling liquid is taken into the syringe 62 and the valve 72 is turned to the third position.

As soon as the switch 54 is turned off, the valve 72 is moved into its second position and the syringe 62 is actuated to inject the cooling liquid into the line 76 and inlet passage 22. The initial movement will result in an amount of liquid being displaced into the balloon 20 to increase its inflation to a maximum inflation pressure within the range of 10 to 20 psi, such as a preferred maximum inflation pressure of approximately 16 psi. In this way, the stenosis and arterial region surrounding the balloon 20 is expanded to the desired level only after the stenosis and arterial region have been changed from the normal generally solid state thereof into a softer more moldable state. In this softer more moldable state, expansion can take place with much less likelihood of tearing and fracturing the stenosis and arterial tissue. The increased pressure is also transmitted to the check valve member 94 so that subsequent inward movement of the piston 66 results in the displacement of the inflating and heating liquid within the inlet passage 22 and balloon 20 through the inlet 28 of the outlet passage 24 and finally out past the check valve. After a flow period of approximately 5 seconds, the cooling liquid within the balloon 20 reduces the temperature of the stenosis and arterial region to a temperature near 25° C. At this temperature, the stenosis and the arterial region is changed back into a relatively solid state wherein there is less tendency for the stenosis and arterial region to self-retract when the inflation pressure is relieved. Accordingly, at this time the valve 72 is turned to its first position to permit the cooling liquid to flow out of the inlet passage 22 and deflate the balloon 20 so that the catheter can be removed.

It thus will be seen that the objects of this invention have been fully and effectively accomplished. It will be realized, however, that the foregoing preferred specific embodiments have been shown and described for the purpose of illustrating the functional and structural principles of this invention and are subject to change without departure from such principles. Therefore, this invention includes all modifications encompassed within the spirit and scope of the following claims

What is claimed is:

1. A method for carrying out balloon catheter angioplasty within a coronary artery having a stenosis comprising the steps of:
   positioning the balloon or the catheter within the stenosis of the artery,
   increasing the temperature of the stenosis and artery surrounding the balloon prior to the inflation of the balloon to an inflation extent sufficient to cause outward expansion for a clinically appropriate time period and to a temperature level sufficient to cause a change in the stenosis and surrounding artery from a relatively solid state into a softer and more moldable state and thereafter increasing the inflation of the balloon so that outward expansion occurs within the stenosis and artery in said softer and more moldable state to thus reduce the tendency to fracture during expansion,
   reducing the temperature of the stenosis and surrounding artery while maintaining the expansion by balloon inflation for a clinically appropriate time period and to a temperature level sufficient to re-establish the relatively solid state thereof so as to increase the tendency to maintain the stenosis and artery in the expanded condition; and
   then deflating the balloon and thereafter withdrawing the catheter.

2. A method as defined in claim 1 wherein the inflation of the balloon is accomplished by introducing a preheated liquid within the balloon at a preheated temperature above room temperature.

3. A method as defined in claim 2 wherein during the increase in temperature of the stenosis and artery the balloon is expanded into contact with the stenosis and artery surrounding the balloon by the preheated liquid introduced within the balloon and the increase in temperature of the stenosis and artery is accomplished through conduction from the preheated liquid within the balloon and by electrically heating a resistance element in contact with the preheated liquid within the balloon inflating by completing a circuit through the resistance element and a source of electrical current alternating at a radio frequency.

4. A method as defined in claim 3 wherein the completion of the circuit is accomplished after the beginning of the introduction of the preheated liquid within the balloon and before the balloon is expanded into contact with the stenosis and artery.

5. A method as defined in claim 3 wherein the reduction in temperature is accomplished by replacing the preheated liquid used to inflate the balloon with cooling liquid at a temperature below room temperature.

6. A method as defined in claim 5 wherein the temperature of the cooling liquid is within the range of 0° to 38° C.

7. A method as defined in claim 6 wherein the increase in the inflation pressure of the balloon is to maximum inflation pressure and is accomplished in conjunction with the replacing of the heating and inflating liquid with a cooling liquid.

8. The improvement as defined in claim 7 wherein the cooling is provided for a period sufficient to reduce the tissue temperature to room temperature.

9. The improvement as defined in claim 8 wherein cooling to room temperature is accomplished in approximately 5 seconds.

10. A method for remodeling a body lumen having a stenosis, to expand the stenosis comprising the steps of:
increasing the temperature of the body lumen and stenosis at the region of the stenosis for a time period and to a temperature level sufficient to cause a change in the stenosis and body lumen region from a relatively solid state into a softer and more moldable state and thereafter expanding the stenosis and the body lumen region while in said softer and more moldable state to thus reduce the tendency to fracture during expansion, and
reducing the temperature of the stenosis and body lumen region while maintaining the expansion for a time period and to a temperature level sufficient to re-establish the relatively solid state thereof so as to increase the tendency to maintain the stenosis and body lumen region in the expanded condition.

11. A method as defined in claim 10 wherein said increased temperature level is within the range of 40° to 100° C.

12. A method as defined in claim 11 wherein said temperature level is approximately 70° C.

13. A method as defined in claim 12 wherein the reduced temperature level is approximately 25° C.

14. An angioplasty apparatus for remodeling a body lumen having a stenosis to expand the stenosis comprising
a catheter comprising an elongated body of flexible material having a distal end portion,
an expandable balloon having an interior surrounding said catheter at the distal end portion thereof,
said catheter body having an inlet passage extending longitudinally therethrough from an inlet position therein to an outlet position at said distal end portion and an outlet passage extending longitudinally therethrough from an inlet portion at said distal end portions to an outlet position,
said inlet passage having an outlet opening at said outlet position communicating with the interior of said balloon through which liquid under pressure in said inlet passage can enter the interior of said balloon, said outlet passage having an inlet opening at said inlet position communicating with the interior of said balloon through which liquid under pressure within said balloon can pass from the balloon into the outlet passage,
heating means at the distal end portion of said catheter operable when connected with a source of electrical energy to heat liquid within the interior of said balloon,
wire means extending within the flexible material of said catheter for selectively connecting a remote source of electrical energy with said heating means,
and means operatively connected with the catheter at the inlet and outlet positions of said inlet and outlet passages for (1) introducing a balloon inflating and heating liquid within said inlet passage with an initial pressure sufficient to establish a liquid pressure within said balloon sufficient to inflate the same into contact with an area of stenosis within a body lumen region within which the distal end portion of said catheter is engaged while said wire means connects the electrical energy source to said heating means to operate the same to heat the liquid under pressure within the balloon to a predetermined temperature sufficient to conduct sufficient heat to the body lumen region to change the tissue in the arterial region and stenosis from a relatively solid state into a softer and more moldable state so that while therein an increase in the liquid pressure within the balloon increases the inflation of the balloon and expands the area of stenosis within the body lumen region within a first predetermined time (2) following the expiration of the first predetermined time displacing the balloon inflation and heating liquid within said inlet passage and the interior of said balloon outward through said outlet passage with a cooling liquid while maintaining an inflating pressure within the interior of said balloon for a second predetermined time sufficient to change the tissue in the body lumen region and stenosis into a relatively solid state to thereby enhance the formation of a smooth inner wall in the body lumen region and (3) following the expiration of the second predetermined time relieving the pressure of the liquid within the interior of the balloon sufficient to deflate the same for removal from the body lumen region.

15. An angioplasty apparatus as defined in claim 14 wherein a distal portion of said catheter body is formed with a central opening for moving a guide wire therethrough.

16. An apparatus as claimed in claim 15 wherein said balloon includes an annular wall having one end fixed to the distal end of said catheter body and an opposite end fixed to the distal end portion of said catheter body inwardly of the distal end thereof.

17. An apparatus as claimed in claim 16 wherein said wire means includes a pair of wires fixed within the flexible material of the catheter body, said heating means including a braided sleeve of electrical resistance wire on the distal end portion of said catheter body intermediate the ends of the balloon, said sleeve having ends connected with said pair of wires.

18. An apparatus as claimed in claim 17 wherein the source of electrical energy is an alternating current having a cycle within the radio frequency range.

19. An apparatus as claimed in claim 18 wherein said means connected with said inlet and outlet passages includes a syringe pump and a check valve.

20. Apparatus for remodeling a body lumen having a stenosis to expand the stenosis comprising:

a catheter, means connected with said catheter for (1) increasing the temperature of the body lumen and stenosis at the region of the stenosis for a time period and to a temperature level sufficient to cause a change in the stenosis and body lumen region from a relatively solid state into a softer and more moldable state and (2) thereafter expanding the stenosis and the body lumen region while in said softer and more moldable state to thus reduce the tendency to fracture during expansion, and means connected with said catheter for reducing the temperature of the stenosis and body lumen region while maintaining the expansion for a time period and to a temperature level sufficient to re-establish the relatively solid state thereof so as to increase the tendency to maintain the stenosis and body lumen region in the expanded condition.

* * * * *